US007122179B2

(12) United States Patent
Kappe et al.

(10) Patent No.: US 7,122,179 B2
(45) Date of Patent: Oct. 17, 2006

(54) LIVE GENETICALLY ATTENUATED MALARIA VACCINE

(75) Inventors: Stefan H. I. Kappe, Seattle, WA (US); Kai-Uwe C. Matuschewski, Heidelberg (DE); Ann-Kristin Mueller, Dossenheim (DE)

(73) Assignees: Seattle Biomedical Research Institute, Seattle, WA (US); Ruprecht-Karls-Universität Heidelberg, Heidelberg (DE)

( * ) Notice: Subject to any disclaimer, the term of this patent is extended or adjusted under 35 U.S.C. 154(b) by 0 days.

(21) Appl. No.: 11/078,200

(22) Filed: Mar. 11, 2005

(65) Prior Publication Data
US 2005/0226896 A1 Oct. 13, 2005

Related U.S. Application Data

(63) Continuation of application No. PCT/US04/43023, filed on Dec. 20, 2004.

(60) Provisional application No. 60/633,242, filed on Dec. 3, 2004, provisional application No. 60/631,228, filed on Nov. 26, 2004, provisional application No. 60/605,014, filed on Aug. 27, 2004, provisional application No. 60/531,479, filed on Dec. 19, 2003.

(51) Int. Cl.
*A01N 63/00* (2006.01)
*A01N 65/00* (2006.01)
(52) U.S. Cl. ............... 424/93.1; 424/93.2; 424/93.21; 424/93.7
(58) Field of Classification Search ........... 424/93.1, 424/93.2, 93.21, 93.7
See application file for complete search history.

(56) References Cited

U.S. PATENT DOCUMENTS

| 4,681,762 A | 7/1987 | Oeschger et al. |
| 6,656,479 B1 | 12/2003 | Brake et al. |

FOREIGN PATENT DOCUMENTS

| WO | WO 95/07094 A1 | 3/1995 |
| WO | WO 00/08165 A1 | 2/2000 |
| WO | WO 2004/026903 A2 | 4/2004 |
| WO | WO 2004/045559 A2 | 6/2004 |

OTHER PUBLICATIONS

Butler, D., "Mosquito Production Mooted as Fast Track to Malaria Vaccine," *Nature* 425:437, Oct. 2, 2003.
Doolan, D.L., and S.L. Hoffman, "The Complexity of Protective Immunity Against Liver-Stage Malaria," *The Journal of Immunology* 165:1453-1462, 2000.
Fandeur, T., et al., "Protection of Squirrel Monkeys Against Virulent *Plasmodium falciparum* Infections by Use of Attenuated Parasites," *Infection and Immunity* 60(4):1390-1396, Apr. 1992.
Guerin-Marchand, C., et al., "A Liver-Stage-Specific Antigen of *Plasmodium falciparum* Characterized by Gene Cloning," *Nature* 329:164-167, Sep. 10, 1987.
Hoffman, S., "Save the Children," *Nature* 430:940-941, Aug. 19, 2004.
Hoffman, S.L., and D.L. Doolan, "Malaria Vaccines-Targeting Infected Hepatocytes," *Nature Medicine* 6(11):1218-1219, Nov. 2000.
Hoffman, S.L., et al., "Protection of Humans Against Malaria by Immunization With Radiation-Attenuated *Plasmodium falciparum* Sporozoites," *The Journal of Infectious Diseases* 185:1155-1164, Apr. 15, 2002.
James, S., and L. Miller, "Malaria Vaccine Development: Status Report," Niaid.nih.gov, Jan. 5, 2001, <http://www.niaid.nih.gov/dmid/malaria/malariavac.htm> [retrieved Oct. 15, 2004].
Kaiser, K., et al., "Differential Transcriptome Profiling Identifies *Plasmodium* Genes Encoding Pre-Erythrocytic Stage-Specific Proteins," *Molecular Microbiology*, 2004, pp. 1221-1232.
Kappe, S.H.I., et al., "*Plasmodium* Sporozoite Molecular Cell Biology," *Annu. Rev. Cell Dev. Biol.* 20:29-59, 2004.
Luke, T.C., and S.L. Hoffman, "Rationale and Plans for Developing a Non-Replicating, Metabolically Active, Radiation-Attenuated *Plasmodium falciparum* Sporozoite Vaccine," *The Journal of Experimental Biology* 206:3803-3808, 2003.
Ménard, R., "Knockout Malaria Vaccine?" *Nature* 433:113-114, Jan. 13, 2005.
Mueller, A.-K., et al., "*Plasmodium* Liver Stage Developmental Arrest by Depletion of a Protein at the Parasite-Host Interface," *PNAS* 102(8):3022-3027, Feb. 22, 2005.
"Parasitic and Tropical Infections," *The Jordan Report: Accelerated Development of Vaccines*, National Institutes of Health, 2000, pp. 25-30.
Scheller, L., and A.F. Azad, "Maintenance of Protective Immunity Against Malaria by Persistent Hepatic Parasites Derived From Irradiated Sporozoites," *Proc. Natl. Acad. Sci. USA* 92:4066-4068, Apr. 1995.
Silvie, O., et al., "Effects of Irradiation on *Plasmodium falciparum* Sporozoite Hepatic Development: Implications for the Design of Pre-Erythrocytic Malaria Vaccines," *Parasite Immunology* 24(4):221-223, Apr. 2002
Suzuki, M., et al., "An Alternative Approach to Malaria Vaccine With a Permanent Attenuated Mutant From a High Virulence Plasmodium Berghei Strain," *Zentralbl. Bakteriol. Mikrobiol. Hyg.* 264(3-4):319-325, May 1987. (Abstract provided). .

(Continued)

*Primary Examiner*—Mark Navarro
(74) *Attorney, Agent, or Firm*—Christensen O'Connor Johnson Kindness PLLC; Thomas F. Broderick; Karen Blöchlinger

(57) ABSTRACT

Method for inoculating a vertebrate host against malaria, by administering to the host a live *Plasmodium* organism that is genetically engineered to disrupt a gene whose expression is up-regulated in liver stage parasites and whose function is not required for entry into hose hepatocytes.

1 Claim, 1 Drawing Sheet

OTHER PUBLICATIONS

Waters, A.P., et al., "Malaria Vaccines: Back to the Future?," *Science 307*:528-530, Jan. 28, 2005.

Worthey, E.A., and P.J. Myler, Invited review, "*Protozoan genomes*: Gene Identification and Annotation," *International Journal for Parasitology 35*:495-512, 2005.

Ménard, R., et al., "Circumsporozoite Protein Is Required for Development of Malaria Sporozoites in Mosquitoes," *Nature 385*(6614):336-340, Jan. 1997.

Ménard, R., and C. Janse, "Gene Targeting in Malaria Parasites," *METHODS: A Companion to Methods in Enzymology 13*(2):148-157, Oct. 1997.

Matuschewski, K., et al., Infectivity-Associated Changes in the Transcriptional Repertoire of the Malaria Parasite Sporozite Stage, *Journal of Biological Chemistry 277*(4):41948-41953, Nov. 2002.

Mueller, A.-K., et al., Genetically Modified *Plasmodium* Parasites as a Protective Experimental Malaria Vaccine, *Nature 433*(7022):164-167, Jan. 13, 2005.

Sultan. A.A., et al., "TRAP Is Necessary for Gliding Motility and Infectivity of *Plasmodium sporozoites*," *Cell 90*(3):511-522, Aug. 8, 1997.

van Dijk, M.R., et al., "A Central Role for P48/45 in Malaria Parasite Male Gamete Fertility," *Cell 104*(1);153-164, Jan. 12, 2001.

SEQUENCE LISTING

<160> NUMBER OF SEQ ID NOS: 18

<210> SEQ ID NO 1
<211> LENGTH: 31
<212> TYPE: DNA
<213> ORGANISM: Plasmodium berghei

<400> SEQUENCE: 1
gggtacccgc attagcataa catctcattg g                         31

<210> SEQ ID NO 2
<211> LENGTH: 31
<212> TYPE: DNA
<213> ORGANISM: Plasmodium berghei

<400> SEQUENCE: 2
caagcttgct ttcatatatt tgttatttgt c                         31

<210> SEQ ID NO 3
<211> LENGTH: 27
<212> TYPE: DNA
<213> ORGANISM: Plasmodium berghei

<400> SEQUENCE: 3
ggaattccca tatgtttgtg taacatc                              27

<210> SEQ ID NO 4
<211> LENGTH: 31
<212> TYPE: DNA
<213> ORGANISM: Plasmodium berghei

<400> SEQUENCE: 4
ctctagagtg tgcttaaatg tttctttaaa c                          31

<210> SEQ ID NO 5
<211> LENGTH: 31
<212> TYPE: DNA
<213> ORGANISM: Plasmodium berghei

<400> SEQUENCE: 5
cggaattcat catattacta attttcgggg g                          31

<210> SEQ ID NO 6
<211> LENGTH: 36
<212> TYPE: DNA
<213> ORGANISM: Plasmodium berghei

<400> SEQUENCE: 6
tccccgcggt tattccatgt tataaacgtt atttcc                     36

<210> SEQ ID NO 7
<211> LENGTH: 23
<212> TYPE: DNA
<213> ORGANISM: Plasmodium berghei

<400> SEQUENCE: 7
cccgcacgga cgaatccaga tgg                                   23

<210> SEQ ID NO 8
<211> LENGTH: 32
<212> TYPE: DNA
<213> ORGANISM: Plasmodium berghei

<400> SEQUENCE: 8
cccaagctta gtttgcatat acggctgctt cc                         32

<210> SEQ ID NO 9
<211> LENGTH: 31
<212> TYPE: DNA
<213> ORGANISM: Plasmodium berghei

<400> SEQUENCE: 9
cggaattctg gattcatttt ttgatgcatg c                          31

<210> SEQ ID NO 10
<211> LENGTH: 21
<212> TYPE: DNA
<213> ORGANISM: Plasmodium berghei

<400> SEQUENCE: 10
gtaatacgac tcactatagg c                                     21

<210> SEQ ID NO 11
<211> LENGTH: 29
<212> TYPE: DNA
<213> ORGANISM: Plasmodium berghei

<400> SEQUENCE: 11
gaattctgga ttcatttttt gatgcatgc                             29

-continued

```
<210> SEQ ID NO 12
<211> LENGTH: 34
<212> TYPE: DNA
<213> ORGANISM: Plasmodium berghei

<400> SEQUENCE: 12
ggggtacctt tattcagacg taataattat gtgc                                34

<210> SEQ ID NO 13
<211> LENGTH: 38
<212> TYPE: DNA
<213> ORGANISM: Plasmodium berghei

<400> SEQUENCE: 13
aaaactgcag ataattcatt atgagtagtg taattcag                            38

<210> SEQ ID NO 14
<211> LENGTH: 34
<212> TYPE: DNA
<213> ORGANISM: Plasmodium falciparum

<400> SEQUENCE: 14
ccccaagctt aagtttgcat atacggctgc ttcc                                34

<210> SEQ ID NO 15
<211> LENGTH: 27
<212> TYPE: DNA
<213> ORGANISM: Plasmodium falciparum

<400> SEQUENCE: 15
gagtaatata atgtgtaatg catatgg                                        27

<210> SEQ ID NO 16
<211> LENGTH: 24
<212> TYPE: DNA
<213> ORGANISM: Plasmodium falciparum

<400> SEQUENCE: 16
gagaccttca tttcaaaaag gaag                                           24

<210> SEQ ID NO 17
<211> LENGTH: 30
<212> TYPE: DNA
<213> ORGANISM: Plasmodium falciparum

<400> SEQUENCE: 17
caaatgaaaa cttggaaata atcagacgag                                     30

<210> SEQ ID NO 18
<211> LENGTH: 32
<212> TYPE: DNA
<213> ORGANISM: Plasmodium falciparum

<400> SEQUENCE: 18
gtattatgct taaattggaa aaaagtttga ag                                  32
```

LIVE GENETICALLY ATTENUATED MALARIA VACCINE

CROSS-REFERENCES TO RELATED APPLICATIONS

This application is a continuation of International Application No. PCT/US04/043023, filed Dec. 20, 2004, which claims the benefit of U.S. Provisional Application No. 60/531,479, filed Dec. 19, 2003, and U.S. Provisional Application No. 60/631,228, filed Nov. 26, 2004; and also claims the benefit of U.S. Provisional Application No. 60/633,242, filed Dec. 3, 2004, and U.S. Provisional Application No. 60/605,014, filed Aug. 27, 2004, all of which are incorporated herein by reference.

STATEMENT OF GOVERNMENT LICENSE RIGHTS

Research leading to the present invention was supported, at least in part, under RO1 A053709 awarded by the National Institutes of Health. The Government may have certain rights in the invention.

The discovery was also supported by the research focus "Tropical Medicine Heidelberg" of the Medical Faculty of Heidelberg University and the Deutsche Forschungsgemeinschaft.

FIELD OF THE INVENTION

This invention relates to live genetically modified *Plasmodium* organisms and their use as immunospecific immunoeffectors for vaccination purposes.

BACKGROUND OF THE INVENTION

Malaria has a tremendous impact on human health, killing millions annually and the disease is a major impediment for social and economic development of nations in malaria-endemic areas, particularly in sub-Saharan Africa (1, see the appended Citations). Malaria is a mosquito-borne disease that is transmitted by inoculation of the *Plasmodium* parasite sporozoite stage. Sporozoites invade hepatocytes (2), transform into liver stages, and subsequent liver stage development ultimately results in release of pathogenic merozoites (3).

Because an effective 'subunit' malaria vaccine has remained elusive and the complexity of the malaria parasite *Plasmodium* might preclude the successful development of such a vaccine, whole organism vaccine approaches against malaria have lately found renewed interest (4). The feasibility of such a vaccine has been demonstrated in animal models and subsequently in humans by induction of sterile protective immunity through inoculation with irradiation-attenuated parasites (5, 6). Liver stages are a prime malaria vaccine target because they can be completely eliminated by sterilizing immune responses, thereby preventing malaria infection (7). The recent availability of complete *Plasmodium* genome sequences (8, 9) may now permit the development of live-attenuated parasites by more precise and defined genetic manipulations (10).

Using expression profiling, we identified genes that are specifically expressed during the pre-erythrocytic part of the parasite life cycle (11, 12). A number of pre-erythrocytic genes named UIS (up-regulated in infective sporozoites) also showed up-regulation in sporozoites when they gain infectivity for the mammalian host (11).

SUMMARY OF THE INVENTION

Here we show by reverse genetics that selected individual genes, exemplified by UIS3 (up-regulated in infective sporozoites gene 3) and UIS4, are essential for early liver stage development: uis3(−) and uis4(−) sporozoites infect hepatocytes but are no longer able to establish blood stage infections in vivo and thus do not lead to disease. The invention thereby provides the first live *Plasmodium* organisms that are genetically engineered to disrupt liver-stage-specific gene functions.

Surprisingly, immunization with either uis3(−) or uis4(−) sporozoites confers complete protection against infectious sporozoite challenge in a rodent malaria model. This protection is sustained and stage-specific. These findings provide the first genetically attenuated whole organism malaria vaccines.

Thus, the invention provides a method for inoculating a vertebrate host against malaria, by administering to the host a live *Plasmodium* organism that is genetically engineered to disrupt a liver-stage-specific gene function. The invention further provides a vaccine composition comprising a live *Plasmodium* organism that is genetically engineered to disrupt a liver-stage-specific gene function. In addition, the invention provides the use of a vaccine composition comprising a live *Plasmodium* organism that is genetically engineered to disrupt a liver-stage-specific gene function. The invention also provides for production of a vaccine composition, by suspending and packaging the subject engineered *Plasmodium* organisms in a suitable pharmaceutically acceptable carrier solution.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
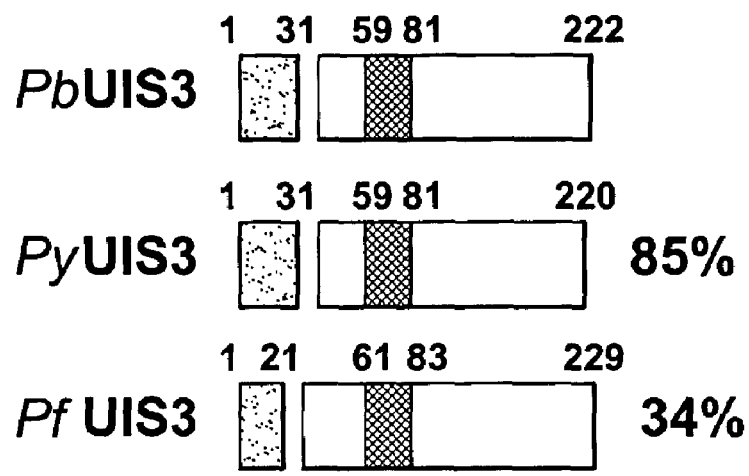
FIG. 1 depicts the primary structure of *Plasmodium* UIS3 proteins, as discussed in Examples 1 and 3. Predicted cleavable signal peptides and transmembrane spans are indicated with stippled and cross-hatched boxes, respectively. Amino acid identities of the *P. yoelii* and *P. falciparum* UIS3 orthologues (EAA22537 and PF13_0012, respectively) are indicated as percentage of identical residues compared with the *P. berghei* sequence.

The invention provides a method for inoculating a vertebrate host against a *Plasmodium* parasite, by administering to the host a live *Plasmodium* organism that is genetically engineered to disrupt a liver-stage-specific gene function.

By "*Plasmodium* parasite" or "*Plasmodium* organism" is meant any member of the protozoan genus *Plasmodium*, including the four species that cause human malaria: *P. vivax*, *P. malariae*, *P. falciparum*, and *P. ovale*. The corresponding "vertebrate host" is a human or other secondary host that is susceptible to infection by the wild-type *Plasmodium* parasite.

For use as a live anti-malarial vaccine, the *Plasmodium* parasite is genetically engineered to disrupt a liver-stage-specific gene function. The term "disrupt liver-stage-specific gene function" or "disrupt LS-specific gene function" means interfering with an LS-specific gene function such as to completely or partially inhibit, inactivate, attenuate, or block the LS-specific gene function, for example, by gene disruption or influencing transcription, translation, protein folding, and/or protein activity. The term "liver-stage-specific gene function" or "LS-specific gene function" refers to a function that is required in liver stage parasites to ultimately produce infectious merozoites and establish the erythrocytic stage of the life cycle, but that is not required for entry into host hepatocytes or, preferably, maintenance of the parasite in asexual blood cell stages and production of infective sporozoites in mosquitoes.

Malaria infection is initiated by *Plasmodium* sporozoites in the salivary glands of mosquitoes. These sporozoites invade hepatocytes of the vertebrate host and differentiate into liver stage (LS) forms. After a few days the LS parasites produce several thousand merozoites that are released from the hepatocytes and invade erythrocytes to start the blood stage cycle that causes malaria disease. According to the invention, the *Plasmodium* parasite is genetically engineered to disrupt at least one LS-specific gene function such that the genetically engineered parasites remain capable of invading hepatocytes but cannot produce merozoites that can establish blood stage infections. Of course, pursuant to this disclosure, more than one LS-specific gene function can be disrupted (such as by creating, for example, double knockouts) as such redundancy may ensure an additional degree of protection against parasitemia.

Pursuant to this disclosure, an LS-specific gene function may be identified using routine methodology that is standard in the art. For example, an LS-specific gene function may be identified by assessing the function of genes whose expression is up-regulated in liver-stage parasites ("LS-up-regulated genes"). For example, genes whose expression is up-regulated in liver-stage parasites may be expressed at higher levels in liver-stage parasites than, e.g., in the sporozoite population that emerges from mosquito mid-gut oocysts. Up-regulation of expression of such genes may also be observed in mature, infective salivary gland sporozoites (like in the UIS4 and UIS3 genes discussed in the Examples below). Well-known methods for differential transcriptional profiling, including, but not limited to, subtractive hybridization screens, differential display, and genome-wide microarray analyses, may be used for identifying genes whose expression is up-regulated in liver-stage parasites. Such methods have been previously used to analyze infectivity-associated changes in the transcriptional repertoire of sporozoite-stage parasites (11) and to identify *Plasmodium* genes that encode pre-erythrocytic stage-specific proteins (12). For example, suppression subtractive hybridization permits selective enrichment of differentially regulated cDNAs of high and low abundance through a combination of hybridization and polymerase chain reaction (PCR) amplification protocols that allow the simultaneous normalization and subtraction of the cDNA populations. Suppression subtractive hybridization has been used to analyze transcriptional differences between non-infective and infective sporozoites and to identity genes controlling infectivity to the mammalian host (11). This procedure has permitted the identification of LS-up-regulated genes, including but not limited to the UIS3 and UIS4 genes disrupted in the Examples below. Suppression subtractive hybridization of *Plasmodium* salivary gland sporozoites versus merozoites has also been used to identify stage-specific pre-erythrocytic transcripts (12). Differential expression of candidate LS-specific genes may be confirmed using methods that are standard in the art, including dot blots, reverse transcriptase PCR (RT-PCR), immunoblotting, immunofluorescence microscopy, and/or microarray expression analyses.

In some embodiments of the invention, LS-specific gene functions are identified by analyzing the function of LS-up-regulated genes, as further described below. However, not all genes with an LS-specific gene function are necessarily LS-up-regulated genes. Thus, genes whose expression is not up-regulated in LS forms may nevertheless possess an LS-specific gene function.

Interference with a liver-specific function may also be achieved by LS-specific overexpression of an inhibitory factor. This factor may be inserted by reverse genetics methods into a pseudogene, i.e., one that is not essential for parasite survival at any time point during the life cycle (47). The inhibitory factor should not confer toxicity to the parasite but rather act in arresting LS development. Such a factor may include, but is not limited to, inhibitors of cell-cycle progression and/or ubiquitin-mediated proteolysis, and/or factors that interfere with post-transcriptional control of gene-expression.

LS-specific gene functions may be identified by analyzing the phenotype of parasites in which one or more gene functions have been disrupted. Several methods for disrupting gene functions in *Plasmodium* are well-known in the art and may be used in the practice of the invention. Such methods include, but are not limited to, gene replacement by homologous recombination, antisense technologies, and RNA interference. For example, methods of gene targeting for inactivation or modification of a *Plasmodium* gene by homologous recombination have been established (13). Such methods were herein successfully used to disrupt LS-specific gene functions, as described in Examples 1 and 2. Antisense technology has also been successfully used for disrupting *Plasmodium* gene functions. For example, exogenous delivery of phosphorothioate antisense oligonucleotides against different regions of the *P. falciparum* topoisomerase II gene result in sequence-specific inhibition of parasite growth (14). Similarly, transfection of an antisense construct to the *Plasmodium falciparum* clag9 gene, which had been shown to be essential for cytoadherence by targeted gene disruption, resulted in a 15-fold reduction in cytoadherence compared to untransfected control parasites (15).

Another exemplary technology that may be used in the practice of the invention to disrupt LS-specific gene functions is RNA interference (RNAi) using short interfering RNA molecules (siRNA) to produce phenotypic mutations in genes. RNAi has been used as a method to investigate and/or validate gene function in various organisms, including plants, *Drosophila*, mosquitoes, mice, and *Plasmodium* (see, e.g., 37–44). In *Plasmodium*, RNAi has been used, for example, to demonstrate the essential role of a PPI serine/threonine protein phosphatase (PfPP1) from *P. falciparum* (41). RNAi has also been used to inhibit *P. falciparum* growth by decreasing the level of expression of the gene encoding dihydroorotate dehydrogenase (42) and by blocking the expression of cysteine protease genes (43). In the mouse malaria model, RNAi has been used to inhibit gene expression in circulating *P. berghei* parasites in vivo (44). These studies have demonstrated the use of RNAi as an effective tool for disrupting gene function in *Plasmodium* organisms.

The gene disruption approaches described above (for example, gene targeting by homologous recombination, antisense, and RNAi) have been used successfully to investigate the function of virtually all genes in an organism's genome. For example, the availability of sequenced genomes has enabled the generation of siRNA libraries for use in large-scale RNAi studies to screen for genes that are involved in various processes, such as developmental pathways or stages (see, e.g., 45 and 46). Such screens may be used in the practice of the invention to identify LS-specific gene functions in *Plasmodium*. Assays that may be used for identifying LS-specific gene functions include, but are not limited to, phenotypic analyses such as the phenotypic assays described in Examples 1 and 2. The term "phenotypic analysis" includes all assays with vital recombinant parasites that are generated in a wild type, fluorescent or any other transgenic reporter background. Assays may be performed in vivo, with cultured cells, in in vitro development assays or any other system that provides a read-out for LS development.

The engineered *Plasmodium* organisms in which an LS-specific gene function has been disrupted are typically grown in cell culture or animals, expanded in the mosquito host, and harvested as sporozoites for use in vaccines (see, e.g., 16).

The subject vaccine compositions are produced by suspending the attenuated live *Plasmodium* organisms in a pharmaceutically acceptable carrier. Suitable pharmaceutically acceptable carriers include sterile water or sterile physiological salt solution, particularly phosphate buffered saline (PBS), as well known in the art.

Vaccines according to the invention can be administered, e.g., intradermally, subcutaneously, intramuscularly, intraperitoneally, and intravenously.

Dosage is empirically selected to achieve the desired immune response in the host. By "immune response" is meant an acquired and enhanced degree of protective immunity, preferably complete or sterile protection, against subsequent exposure to wild-type *Plasmodium* sporozoites. In the working examples described below, sterile protection was achieved following three vaccinations with 10,000 live genetically attenuated sporozoites per inoculation.

DETAILED TECHNICAL DESCRIPTION

Background. Radiation-attenuated sporozoites are a singular model that achieves sterile, protective immunity against malaria infection.

Malaria causes more than 300 million clinical cases and more than 1 million death annually. The disease has a severe negative impact on the social and economic progress of developing nations. Transmission of the malaria parasite *Plasmodium* to the mammalian host occurs when infected mosquitoes bloodfeed and inoculate the sporozoite stage (spz). After entering the bloodstream, spzs are quickly transported to the liver where they extravasate and invade hepatocytes (2). Within hepatocytes, spzs transform into liver stages (LS) (also called exo-erythrocytic forms, EEFs). LS parasites grow, undergo multiple rounds of nuclear division and finally produce thousands of merozoites (17, 18). Merozoites released from the liver rapidly invade red blood cells and initiate the erythrocytic cycle, which causes malaria disease. A protective malaria vaccine would have tremendous impact on global health but despite over a century of efforts, no vaccine has been developed that confers prolonged protection. Yet, we have known for more than 35 years that sterile protracted protection against malaria infection is possible.

Immunization of mice with radiation-attenuated rodent model malaria spzs (gamma-spzs) induces sterile immunity against subsequent infectious spz challenge, thus completely preventing the initiation of blood stage infection from the liver (5). Importantly, based on these findings it was later shown that immunization of humans with gamma-*P. falciparum* spzs completely protected greater than 93% of human recipients (13 of 14) against infectious spz challenge and that protection can last for at least 10 months (6). Gamma-spzs retain the capacity to infect the liver of the mammalian host and invade hepatocytes (19–20). However, LS derived from gamma-spzs suffer arrested development and thus do not produce red blood cell-infectious merozoites. Although, the inoculated stage is the spz, the main immune target is the infected hepatocyte harboring the LS (21). Protective immunity is spz-dose and radiation-dose dependent: greater than 1000 immunizing bites from *P. falciparum*-infected mosquitoes exposed to 15,000–20,000 rads of gamma radiation is required to protect the majority of subjects exposed to infectious spz challenge (6). Mosquitoes inoculate between 10–100 spzs during a bite (22–23). Therefore, the total spz dose for complete protection comes to 10,000–100,000. Importantly, immunization with over-irradiated spzs or heat-inactivated spzs fails to induce protection, indicating that the spz must remain viable for some time after inoculation and must progress to a liver stage that induces protection (6, 24). On the basis of observations in the rodent malaria model, protracted protective immunity may depend on sufficient expression of LS antigen (Ag), because treatment with primaquine, a drug that kills LS, aborts the development of protection (21). Importantly, protection induced by *P. falciparum* gamma-spzs is strain-transcending: inoculation with gamma-spzs of one parasite strain confers protection against heterologous strains (6).

Although we have learned much about spz gene expression in the last few years (25–27), the LS as the putative immunological target(s) of gamma-spzs induced protection have so far completely eluded gene expression analysis because of their inherent experimental inaccessibility. We currently know only one liver stage-specific Ag, liver stage antigen-1 (LSA-1) (28). Thus, the fine Ag specificity of lymphocytes participating in protective immunity remains unknown in humans, because the Ags expressed by LS parasites remain unknown.

Feasibility to create genetically attenuated *Plasmodium* Liver Stages. To generate genetically attenuated *Plasmodium* LS that are defective only in LS development a stage-specific gene that plays an essential and exclusive role at this stage needs to be disrupted. The gene should not be essential during the blood stage cycle given that *Plasmodium* is haploid and transfection is done with asexual blood stages and the mutant parasites are typically maintained as blood stages (13). We previously employed transcription-profiling based on the prediction that infectious *Plasmodium* spzs residing in the mosquito salivary glands are uniquely equipped with transcripts required for hepatocyte invasion and subsequent development of the LS (11). Next, we screened for transcripts that are specific for pre-erythrocytic and absent from blood cell stages (12). The combined screens identified two abundant salivary-gland-spz-enriched transcripts that are absent from blood stages, termed UIS3 and UIS4 (for upregulated in infectious spzs). Cell biological studies have shown that both encoded proteins locate to the parasitophorous vacuole, the parasite-derived organelle where replication and schizogony takes place (data not shown).

Gene knockouts using insertion and replacement strategies have now revealed that both genes are necessary for LS development (see Examples 1 and 2 below). Both proteins are normally expressed in spzs (data not shown), but uis3(−) and uis4(−) parasites develop normal spzs and these invade hepatocyte normally. However, uis3(−) and uis4(−) LS arrest in intermediate-LS development and do not produce late LS (data not shown). Therefore, both UIS3 and UIS4 have LS-specific gene functions. Remarkably, animals infected by natural bite or intravenously with doses of up to 10,000 spzs do not become patent, confirming that both genes play vital roles in successful completion of the *Plasmodium* life cycle (see Tables 1 and 2 below). Therefore, we succeeded in generating the first genetically attenuated LS. Based on these discoveries we and others can now advance and test various LS-up-regulated genes identified by microarray analysis for their importance in LS development. We predict that more LS-up-regulated genes will turn out to be essential for LS development (i.e., to possess LS-specific gene functions), especially uniquely expressed genes given the remarkable capacity of the parasite to develop from a single spz to more than 10,000 daughter merozoites. Such LS-up-regulated genes can be similarly disrupted to produce additional live vaccine candidates, as described herein.

Representative embodiments of the present invention are described in the following two working examples.

EXAMPLE 1

This first Example was published by *Nature* AOP on Dec. 5, 2004 (29).

We hypothesized that inactivation of UIS genes for which expression is restricted to pre-erythrocytic stages could lead to attenuation of the liver stage parasite, without affecting the blood stages or mosquito stages. We focused on a gene called UIS3 that encodes a small conserved transmembrane protein (FIG. 1). UIS3 was expressed in infectious sporozoites (12) and we determined that it was also expressed after sporozoite infection of livers in vivo (data not shown). UIS3 of rodent malaria parasites (accession number EAA22537) and UIS3 of the human malaria parasite *P. falciparum* (Pf13_0012) show 34% amino acid sequence identity (FIG. 1). Because the rodent malaria parasites such as *P. berghei* (Pb) are excellent models to study *Plasmodium* liver stage and pre-erythrocytic immunity we pursued investigation of UIS3 in this species.

Figure 2:
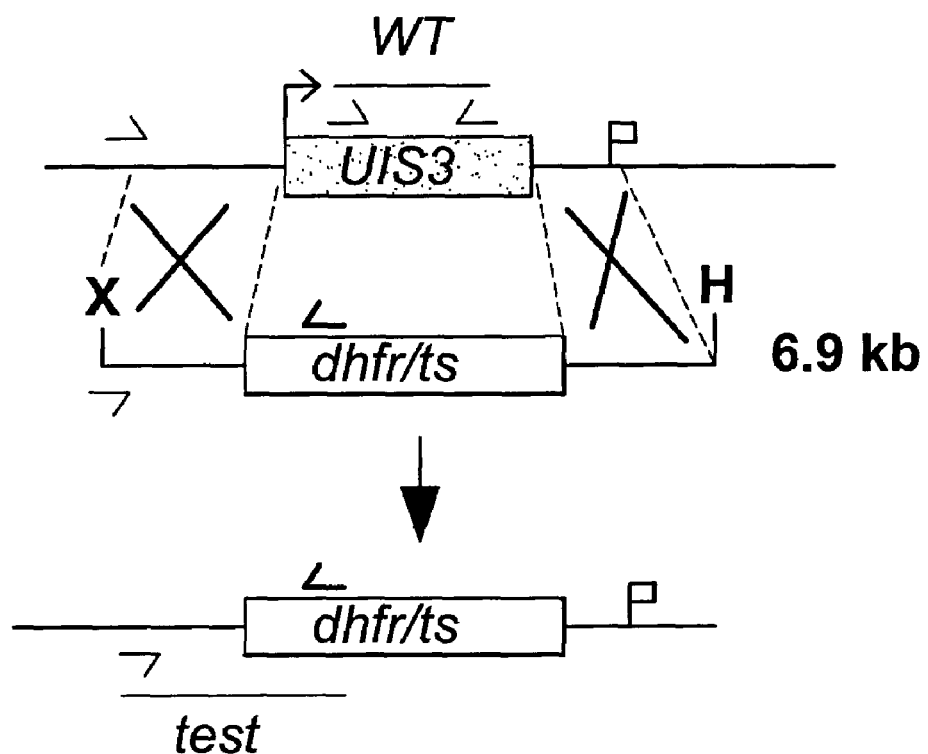
FIG. 2 depicts the replacement strategy used to generate the uis3(−) parasite described in Example 1. The wild-type (WT) UIS3 genome locus is targeted with an EcoRI/HindIII-linearized replacement plasmid containing the 5' and 3' untranslated regions of the UIS3 open reading frame (ORF) and the *Toxoplasma gondii* dhfr/ts-positive selectable marker. Upon a double crossover event the UIS3 ORF is replaced by the selection marker. Replacement-specific test primer combinations are indicated by arrows, and expected fragments are shown as lines.

The endogenous PbUIS3 gene was deleted using an established replacement strategy (13) (FIG. 2). After transfection, parental blood stage parasites were used to obtain clonal parasite lines designated uis3(−) that contained exclusively the predicted locus deletion (data not shown). uis3(−) parasites showed normal asexual blood stage growth and normal transmission to the *Anopheles* mosquito vector (data not shown). Within the mosquito uis3(−) sporozoites developed normally in midgut oocycts and infected the salivary glands in numbers comparable to wildtype (WT) sporozoites (data not shown). Reverse transcriptase (RT)-PCR confirmed lack of UIS3 expression in uis3(−) sporozoites (data not shown). uis3(−) sporozoites showed typical gliding motility, a form of substrate-dependant locomotion that is critical for sporozoite transmission and infectivity (30) (data not shown). They also retained their host cell invasion capacity of cultured hepatoma cells at levels comparable to WT parasites (data not shown).

Intracellular uis3(−) sporozoites initiated the typical cellular transformation process that leads to de-differentiation of the banana-shaped elongated sporozoite to a spherical liver trophozoite (17, 31) (data not shown). In marked contrast, uis3(−) parasites showed a severe defect in their ability to complete transformation into liver trophozoites (data not shown). Only a small fraction of uis3(−) parasites developed into spherical early liver stages, that in addition appeared consistently smaller than the corresponding WT forms. Consequently, mutant parasites lacked the capacity to progress to mature liver schizonts (data not shown). Based on this extreme developmental defect observed in vitro, we next tested if uis3(−) sporozoites had lost their capacity to progress through liver stage development and lead to blood stage infections in vivo. Indeed, intravenous injection of up to 100,000 uis3(−) sporozoites failed to induce blood stage parasitemia in young Sprague/Dawley rats which are highly susceptible to *P. berghei* sporozoite infections (data not shown). Control WT sporozoites induced blood stage parasitemia in rats between 3–4 days after injection.

Thus, the observed phenotypic characteristics of uis3(−) parasites, i.e., their ability to invade hepatocytes and their defect in complete liver stage development allowed us to test them as a whole organism vaccine in a mouse/sporozoite challenge model. We intravenously immunized mice with uis3(−) sporozoites using different prime-boost regimens and subsequently challenged the mice by intravenous injection of infectious WT sporozoites (Table 1). Protection was evaluated by blood smear to detect the development of blood stage parasitemia starting two days after sporozoite challenge, the most stringent readout for sterile protection against malaria infection. Priming with 50,000 uis3(−) sporozoites followed by 2 boosts with 25,000 uis3(−) sporozoites completely protected all immunized mice against a challenge with 10,000 WT sporozoites given 7 days after the last boost (Table 1). Complete sterile protection against the same sporozoite challenge dose was also achieved with a similar prime-2 boost protocol using 10,000 uis3(−) sporozoites (Table 1). We next immunized mice using the same prime-boost protocols but challenged with WT sporozoites 4 weeks after the last boost. None of the challenged mice developed blood stage infections and thus enjoyed protracted sterile protection (Table 1). Protracted protection was confirmed by a re-challenge experiment where protected animals were challenged again with a high inoculum of 50,000 infectious sporozoites after two months. All animals remained completely protected. Mice immunized with uis3(−) sporozoites were also completely protected against re-challenge by infectious mosquito bite (Table 1). To determine the level of protection with a reduced immunization dose we tested a prime-single boost protocol with 10,000 uis3(−) sporozoites. Seven out of ten animals enjoyed complete protection, while the remaining three animals became patent after a long delay in patency. Next, a subset of immunized mice was challenged by direct inoculation with blood stage parasites. All animals developed blood stage parasitemia two days after challenge, indicating that the observed protective immunity is not acting against blood stages and thus was specific against pre-erythrocytic stages. Finally, to evaluate a more vaccine-relevant delivery route we immunized mice subcutaneously using a prime-2 boost protocol with 50,000 uis3(−) and 25,000 uis3(−) sporozoites, respectively. All mice were completely protected against subsequent intravenous WT sporozoite challenge.

Our results show that it is possible to develop genetically modified malaria parasites that are completely attenuated at the liver stage, which normally establishes infection of the mammalian host after mosquito transmission. This attenuation was achieved by deletion of a single parasite gene, UIS3. Although UIS3 function remains unknown, uis3(−) parasites clearly lacked the ability to compensate for its loss. The protracted sterile protection against malaria that we observed after immunization with uis3(−) sporozoites in the mouse/sporozoite challenge model provides proof of principle that a genetically modified malaria vaccine is feasible. We identified a UIS3 orthologue (accession number PF13_0012) in the genome of the most lethal human malaria parasite *P. falciparum*. This will allow us to create a genetically attenuated uis3(−) human parasite that can be tested as a vaccine in human/sporozoite challenge models. Together our findings lead the way to the development of a genetically attenuated, protective whole organism malaria vaccine that prevents natural infection by mosquito bite.

Methods: *Plasmodium berghei* transfection. For replacement of PbUIS3 two fragments were amplified using primers: UIS3rep1 for (5' GGGTACCCGCATTAGCATAA-CATCTCATTGG 3') (SEQ ID NO: 1) and UIS3rep2rev (5'CAAGCTTGCTTTCATATATTTGTTATTTGTC 3') (SEQ ID NO: 2) for the 800 bp 3' fragment; and: UIS3rep3 for (5' GGAATTCCCATATGTTTGTGTAACATC 3') (SEQ ID NO: 3) and UIS3rep4rev (5'CTCTAGAGTGTGCT-TAAATGTTTCTTTAAAC 3') (SEQ ID NO: 4) for the 760 bp 5' fragment using *P. berghei* genomic DNA as template. Cloning into the *P. berghei* targeting vector (13) resulted in plasmid pAKM19. To obtain clonal parasite populations, limited dilution series and i.v. injection of one parasite into 15 recipient NMRI mice each was performed. For RT-PCR analysis we dissected $6\times10^5$ uis3(−) and $6\times10^5$ WT salivary gland sporozoites and isolated polyA$^+$ RNA using oligo dT-columns (Invitrogen). For cDNA-synthesis and amplification we performed a two step-PCR using random decamer primers (Ambion) and subsequent standard PCR reactions.

Phenotypical analysis of uis3(−) parasites. *Anopheles stephensi* mosquito rearing and maintenance were under a 14 h light/10 h dark cycle, 75% humidity and at 28° C. or 20° C., respectively. For each experiment, mosquitoes were allowed to blood-feed for 15 min. on anaesthetized NMRI-mice that had been infected with wild-type *P. berghei* NK65 or the uis3(−) clone and were assayed for a high proportion of differentiated gametocytes and microgametocyte-stage parasites capable of exflagellation. Mosquitoes were dissected at days 10, 14, and 17 to determine infectivity, midgut sporozoite and salivary gland sporozoite numbers, respectively. For analysis of sporozoite motility, sporozoites were deposited onto precoated (3% BSA/RPMI 1640) glass coverslips, fixed for 10 min at RT with 4% paraformaldehyde, and incubated using primary antibody against *P. berghei* circumsporozoite protein (anti-PbCSP) (32). To detect liver stages in hepatocytes, $10^3$ Huh7 cells were seeded in eight chamber slides and grown to semiconfluency. *P. berghei* sporozoites were added, incubated 90 min. at 37° C., and washed off. After 8, 12, 15, 24, 36 and 48 h, LS were revealed using primary antibodies against the *P. berghei* heat shock protein 70 (HSP70) (33). To analyze sporozoite invasion a double staining protocol with anti-CSP antibody was used (36). To determine the infectivity of clonal sporozoite populations in vivo young Sprague-Dawley rats were injected intravenously with 100 microliter sporozoite suspension in RPMI 1640. Parasitemia of the animals was checked daily by Giemsa-stained blood smears. The appearance of a single erythrocytic stage represents the first day of patency.

Immunization and parasite challenge experiments. For all experiments female C57BL/6 mice (Charles River Laboratories) at the age of 50 to 80 days were used. For immunization, uis3(−) sporozoites were extracted from salivary glands from infected mosquitoes. Typically, a single infected mosquito contained 20,000 uis3(−) sporozoites. Sporozoites were injected in a volume of 100 microliters intravenously into the tail vein or subcutanously into the neck of animals. Animals were immunized with a single dose of 1 or $5\times10^4$ uis3(−) sporozoites, followed by two boosts of either 1 or $2.5\times10^4$ uis3(−) sporozoites administered i.v. or s.c. The first boost was given 14 days following the immunization, with a second boost following 7 days thereafter, or at time intervals indicated. One set of animals was immunized followed by a single boost with $1\times10^4$ uis3(−) sporozoites each. The animals were then monitored for the parasitemia by daily blood smears. All animals remained blood stage parasite-negative after the first immunization and subsequent boosts. Animals were challenged 7 days up to 1 month after receiving the last boost of uis3(−) sporozoites by intravenous or subcutaneous injection of either $5\times10^4$ or $1\times10^4$ infectious *P. berghei* WT sporozoites. For each set of experiments, at least three naive animals of the same age group were included to verify infectivity of the sporozoite challenge dose. In each naive animal, parasitemia was readily detectable at days three to five after injection by Giemsa-stained blood smears. Protected animals were monitored for at least 14 days and typically up to 1 month. A re-challenge study was performed for one immunization experiment two months after the first challenge with a single dose of $5\times10^4$ infective *P. berghei* WT sporozoites. To test whether uis3(−) immunized mice were protected against re-challenge by natural transmission 10 protected and 5 naive control mice were exposed for 10 min to 10 highly infected mosquitoes that contained an average of 40,000 WT salivary gland sporozoites each. Successful blood-feeding was confirmed by mosquito dissection after the challenge experiment. To confirm stage-specificity of protection, an additional experiment was performed with 10 mice that were fully protected against a challenge with infective sporozoites. All immunized mice and three naive control mice were challenged by intravenous injection of $5\times10^4$ *P. berghei* WT blood stage parasites. All mice were fully susceptible to blood stage inoculations with no differences in patency.

Results: Table 1 below shows that C57B1/6 mice immunized with *P. berghei* uis3(−) sporozoites are completely protected against a challenge with WT *P. berghei* sporozoites.

TABLE 1

| Exp. | Immunization #'s uis3(−) spz. | Boosts: 1st/2nd numbers (day) | Challenge dose (timepoint) | # Protected/ # Challenged (pre-patency) |
|---|---|---|---|---|
| I. | 50,000 | 25,000 (d.14)/ 25,000 (d.21) | 10,000 spz. (d.7) | 10/10 (no infection) |
|  | 10,000 | 10,000 (d.14)/ 10,000 (d.21) | 10,000 spz. (d.7) | 10/10 (no infection) |
|  | — | — | 10,000 spz. | 0/9 (d.3) |

TABLE 1-continued

| Exp. | Immunization #'s uis3(−) spz. | Boosts: 1st/2nd numbers (day) | Challenge dose (timepoint) | # Protected/ # Challenged (pre-patency) |
|---|---|---|---|---|
| II. | 50,000 | 25,000 (d.34)/ 25,000 (d.45) | 10,000 spz. (d.30) | 5/5 (no infection) |
|  | 10,000 | 10,000 (d.34)/ 10,000 (d.45) | 10,000 spz. (d.30) | 5/5 (no infection) |
|  | — | — | 10,000 spz. | 0/6 (d.4.5) |
| IIII. | 50,000 | 50,000 (d.14)/ 10,000 (d.21) | 10 inf. mosq. (d.38) | 5/5 (no infection) |
|  | 10,000 | 10,000 (d.14)/ 10,000 (d.21) | 10 inf. mosq. (d.38) | 5/5 (no infection) |
|  | — | — | 10 inf. mosq. | 0/5 (d.3) |
| IV | 10,000 | 10,000 (d.14)/— | 10,000 spz. (d.7) | 7/10 (d.8) |
|  | — | — | 10,000 spz. | 0/5 (d.3) |
| V. | 50,000 | 25,000 (d.14)/ 25,000 (d.21) | 10,000 blood st. (d.30) | 0/5 (d.2) |
|  | 10,000 | 10,000 (d.14)/ 10,000 (d.21) | 10,000 blood st. (d.30) | 0/5 (d.2) |
|  | — | — | 10,000 blood st. | 0/3 (d.2) |
| VVI. | 50,000 s.c. | 25,000 (d.11) s.c./ 25,000 (d.18) s.c. | 10,000 spz. (d.23) | 5/5 (no infection) |
|  | 50,000 s.c. | 25,000 (d.11) s.c./ 25,000 (d.18) s.c. | 50,000 spz. (d.23) | 5/5 (no infection) |
|  | — | — | 10,000 spz. | 0/6 (d.4.5) |

Notes:
Mice were immunized with *P. berghi* uis3(−) sporozoites. Mice were challenged with infectious *P. berghei* WT sporozoites or blood stages. Mice were from the same age group (50–80 days old) and sporozoites were from the same mosquito batch. Timepoints in column 4 indicate the day of challenge after the final boost. The pre-patent period is defined as the time until the first appearance of a single erythrocytic stage in Giemsa-stained blood smears. Five mice of the Exp. I. group were re-challenged with one dose of 50,000 WT sporozoites 2 months after the first challenge and remained protected.

EXAMPLE 2

This second Example summarizes the following publication: Mueller, A.-K. et al. *Plasmodium* liver stage developmental arrest by depletion of a protein at the parasite-host interface, *Proc. Natl. Acad. Sci. U.S.A.* 102(8):3022–3027, 22 Feb. 2005, which is hereby incorporated by reference.

Here, we disrupted another *Plasmodium* protein with a critical function for complete liver stage development. UIS4 (upregulated in infective sporozoites gene 4) is expressed exclusively in infective sporozoites and developing liver stages. Targeted gene disruption of UIS4 in the rodent model malaria parasite *Plasmodium berghei* generated knockout parasites that complete the malaria life cycle until after hepatocyte invasion. UIS4 knockout parasites transform into early liver stages. However, they are severely impaired in further liver stage development and can only initiate blood stage infections when inoculated at high sporozoite doses. Immunization with UIS4 knockout sporozoites completely protects mice against subsequent infectious wildtype sporozoite challenge. After sporozoite invasion of hepatocytes, UIS4 localizes to the newly formed parasitophorous vacuole membrane that constitutes the parasite-host cell interface and extends as a tubo-vesicular network into the hepatocyte cytoplasm. Together our data demonstrate that depletion of UIS4 results in attenuated liver stage parasites. Genetically attenuated liver stages may induce immune responses, which inhibit subsequent infection of the liver with wildtype parasites.

Generation of uis4(−) parasites: Given that UIS4 is expressed in sporozoites but not in blood stages, we were able to pursue a targeted gene disruption at the blood stages to study the importance of UIS4 for the *Plasmodium* pre-erythrocytic life cycle stages. The endogenous PbUIS4 gene was disrupted using the above-described insertion and replacement strategies (13) (data not shown). The parental blood stage population from the successful transfection was used for selection of clonal parasite lines carrying the gene disruption. We obtained insertion/disruption clones designated uis4(−) and replacement clones designated uis4REP (−) that contained exclusively the predicted mutant locus. The correct replacement event was confirmed by insertion-specific PCR (data not shown). To confirm PbUIS4 deficiency of the mutant parasites we performed RT-PCR and cDNA amplification using polyA$^+$ RNA from salivary gland sporozoites as templates (data not shown). Moreover, Western blot analysis of uis4REP(−) sporozoites did not detect PbUIS4 (data not shown).

*Plasmodium berghei* transfection and genotypic analysis: For gene targeting of PbUIS4 a 582 bp fragment was amplified using primers UIS4INT for (5' CGGAATTCAT-CATATTACTAATTTTCGGGGG 3') (SEQ ID NO: 5) and UIS4INTrev (5' TCCCCGCGGTTATTCCATGT-TATAAACGTTATTTCC 3') (SEQ ID NO: 6) using *P. berghei* genomic DNA as template. Cloning into the *P. berghei* targeting vector (13) resulted in plasmid pAKM15. Parasite transformation and selection was performed as described previously (13). Integration-specific PCR amplification of the uis4(−) locus was achieved using the following primers: test1, *T. gondii* DHFR-TS for (5' CCCGCACG-GACGAATCCAGATGG 3') (SEQ ID NO: 7) and UIS4 test rev (5' CCCAAGCTTAGTTTGCATATACGGCTGCTTCC 3') (SEQ ID NO: 8); test 2, UIS4 test for (5'CGGAATTCTG-GATTCATTTTTTGATGCATGC 3' (SEQ ID NO: 9) and T7 (5' GTAATACGACTCACTATAGGC 3') (SEQ ID NO: 10). For replacement of PbUIS4 two fragments 1 kb and 600 bp were amplified using primers UIS4rep1 for (5' GAAT-TCTGGATTCATTTTTTGATGCATGC 3') (SEQ ID NO:

11) and UIS4rep2rev (5' GGGGTACCTTTATTCAGACG-TAATAATTATGTGC 3') (SEQ ID NO: 12) for the 1 kb fragment and UIS4rep3 for (5' AAAACTGCAGATAAT-TCATTATGAGTAGTGTAATTCAG 3') (SEQ ID NO:13) and UIS4rep4rev (5' CCCCAAGCTTAAGTTTG-CATATACGGCTGCTTCC 3') (SEQ ID NO:14) for the 600 bp fragment using *P. berghei* genomic DNA as template. Cloning into the hDHFR targeting vector (34) resulted in plasmid pAKM17. To detect UIS4 expression in WT and mutant *P. berghei* parasites, $1 \times 10^5$ salivary gland sporozoites were dissolved in 10 microliters SDS sample buffer. UIS4 was visualized on Western blots using the polyclonal UIS4 antisera (12) and horseradish peroxidase-coupled anti-rabbit IgG secondary antibody (Amersham). For RT-PCR analysis we dissected $8 \times 10^5$ uis4(−), $8 \times 10^5$ uis4REP(−) and $4 \times 10^5$ WT salivary gland sporozoites and isolated polyA$^+$ RNA using oligo dT-columns (Invitrogen). For cDNA synthesis and amplification we performed a two step-PCR using random decamer primers (Ambion) and subsequent standard PCR reactions.

Phenotypic analysis of uis4(−) parasites: *Anopheles stephensi* mosquitoes were raised under a 14 h light/10 h dark cycle at 28° C., 75% humidity and were fed on 10% sucrose solution. Blood-feeding and mosquito dissection was as described (35). The number of sporozoites per infected mosquito was determined in a hemocytometer. To analyze sporozoite motility, sporozoites were deposited onto precoated glass coverslips and incubated using primary antibody against *P. berghei* circumsporozoite protein (anti-PbCSP) (35). Bound antibody was detected using Alexa Fluor 488-conjugated anti-mouse antibody (Molecular Probes). To detect liver stages in hepatocytes, *P. berghei* sporozoites were added to subconfluent hepatocytes, incubated 2 h at 37° C., and washed off. After 12, 24, 36 and 48 h, liver stages were revealed using primary antibodies against parasite heat shock protein 70 (HSP70) and a secondary antibody conjugated with Alexa Fluor 488 (Molecular Probes). To analyze sporozoite invasion, $3 \times 10^4$ salivary gland sporozoites were added to subconfluent HepG2 cells and incubated for 90 min at 37° C. The ratio between intracellular and extracellular parasites was visualized using a double staining protocol with the anti-CSP antibody (36) and confocal microscopy. To determine the infectivity of clonal sporozoite populations in vivo, C57/B16 mice were injected intravenously or subcutaneously with 100 microliters sporozoite suspension of WT parasites or knockout parasites in RPMI 1640. Parasitemia of the animals was checked daily by examination of a Giemsa-stained blood smear. The appearance of a single erythrocytic stage represents the first day of patency.

Immunization and parasite challenge experiments: For all experiments female C57BL/6 mice (Charles River Laboratories) aged between 50 and 80 days were used. For immunizations, uis4REP(−) sporozoites were extracted from the salivary glands from infected mosquitoes. Sporozoites were injected in a volume of 100 microliters intravenously into the tail vein of the animals. Animals were immunized with a single dose of 10,000 or 50,000 uis4REP(−) sporozoites, followed by two boosts of either 10,000 or 25,000 uis4REP (−) sporozoites adminstered i.v. The first boost was given 14 days following the immunization, with a second boost following 14 days thereafter. The animals were then monitored for parasitemia by daily blood smears. Only those animals that remained blood stage parasite-negative after the first immunization and subsequent boosts were exposed to a challenge with WT sporozoites. Animals were challenged 10 days after receiving the last boost of uis4REP(−) sporozoites by intravenous injection. All challenges consisted of 50,000 infective *P. berghei* WT sporozoites. For both sets of experiments, 5 naive animals were included to verify infectivity of the sporozoite challenge dose. In each naive animal, parasitemia was readily detectable at day 3 after injection. Starting from day 3 after WT challenge, the uis4REP(−) sporozoite-immunized animals were examined for detectable parasitemia in Giemsa-stained blood smears. Animals did not show a detectable parasitemia within 50 days following the challenge and were considered completely protected.

Results are shown in Table 2 below. Immunization with uis4REP(−) sporozoites confers sterile protection. The fact that a large proportion of mice remained blood stage negative after inoculation with uis4REP(−) sporozoites allowed us to test if immunization with these attenuated sporozoites would protect mice against WT sporozoite challenge. Therefore, we immunized C57/b16 mice with 3 doses of 50,000 or 10,000 uis4REP(−) sporozoites and subsequently challenged the mice, which remained blood stage negative after immunization, with 50,000 infectious WT sporozoites (Table 2). None of the immunized mice developed blood stage infections after challenge and therefore enjoyed complete, sterile protection. Naive mice that were challenged with 50,000 WT sporozoites developed blood stage infections 3 days after inoculation.

Table 2. C57Bl/6 mice immunized with uis4REP(−) sporozoites are completely protected against a challenge with WT sporozoites.

TABLE 2

| Immunization (uis4REP(−) spz.) | Boosts (days after immun./ # of spz.) | # Protected/ # Challenged (prepatency) |
|---|---|---|
| 50,000 | 1$^{st}$ (14/25,000), 2$^{nd}$ (28/25,000) | 8/8 (no infection)[1] |
| none | none | 0/5 (day 3)[2] |
| 10,000 | 1$^{st}$ (14/10,000), 2$^{nd}$ (28/10,000) | 8/8 (no infection)[1] |
| none | none | 0/5 (day 3)[2] |

Notes:
[1]Immunized mice were challenged with 50,000 WT *P. berghei* sporozoites at day 38 after immunization. Mice were from the same age group and sporozoites were from the same mosquito batch. Blood smears were evaluated up to day 50 after challenge.
[2]Naive control mice were from the same age group and challenged with 50,000 WT *P. berghei* sporozoites.

Summary: Our findings demonstrate that malaria parasites harbor genes that are necessary only for successful completion of the pre-erythrocytic mammalian infection, within hepatocytes. We have shown that deletion of two genes individually effectively creates genetically attenuated malaria parasites that infect the liver of the mammalian host but are severely impaired in their ability to further progress through the life cycle and cause malaria disease. Other genes in the *Plasmodium* genome, which are critical for liver stage development, can be identified with the materials, methods, and procedures described herein.

Finally, we have shown here that immunization with UIS3 and UIS4 knockout sporozoites confers complete, sterile protection against subsequent infectious sporozoite challenge in a mouse model. This demonstrates the successful use of genetically attenuated *Plasmodium* parasites as live experimental vaccines. Genetically attenuated human *Plasmodium* parasites may be similarly prepared as whole organism vaccines against malaria.

EXAMPLE 3

This third example describes a representative protocol for making a UIS3-like knockout in *P. falciparum*.

The *P. falciparum* UIS3 gene is targeted for disruption by replacement via a well-established double-crossover recombination strategy (13). The UIS3 locus is replaced by a fragment containing the 5' and 3' untranslated regions of the *P. falciparum* UIS3 open reading frame, each flanking the human dihydrofolate reductase (hdhfr) selectable marker. Sequence data for the *P. falciparum* UIS3 locus were obtained from the PlasmoDB database (www.plasmodb.org). The accession number for the coding sequence of *P. falciparum* UIS3 is PF13_0012 (12) and the location of the exon within chromosome 13 is 123930–124619 on the minus strand. The *P. falciparum* UIS3 rep1 fragment extends from nucleotides 124609–125594, and the rep2 fragment from 122872-123921.

PfUIS3 rep 1 and 2 fragments are amplified from *P. falciparum* 3D7 genomic DNA using Expand polymerase and the following primers: PfUIS3 rep1 forward 5'-GAG-TAATATAATGTGTAATGCATATGG-3' (SEQ ID NO:15) and reverse 5'-GAGACCTTCATTTCAAAAAGGAAG-3' (SEQ ID NO:16); PfUIS3 rep2 forward 5'-CAAAT-GAAAACTTGGAAATAATCAGACGAG-3' (SEQ ID NO:17) and reverse 5'-GTATTATGCTTAAATTG-GAAAAAAGTTTGAAG-3' (SEQ ID NO:18). The sizes of the rep1 and rep2 fragments amplified are 986 and 1051 base pairs, respectively. The PCR conditions are: one cycle of 94° C. for 3 min, followed by thirty cycles of 94° C. for 30 sec, 54.5° C. for 1 min, and 65° C. for 3 min.

The PCR products are digested and cloned into the pHTK (47) vector. Rep1 was cloned into restriction sites BglII and SacII, and rep2 into EcoI and SfoI sites. The PfUIS3 replacement construct is sequenced to confirm correct cloning. Positive selection for transfected parasites carrying the dhfr gene is carried out with the drug WR99210. pHTK contains the gene for thymidine kinase, allowing for negative selection of parasites carrying the plasmid episomally.

A similar protocol may be used for making a knockout of any gene of interest in *P. falciparum* (for example, a UIS4-like gene, accession number NP_700638, PF10_0164), or for making a knockout of such LS-specific genes in other *Plasmodium* organisms. Genomic information, including genomic sequences, ESTs, annotations, automated predictions, SAGE tags, microarray data, mapping data, and open reading frames, for many *Plasmodium* organisms, including, for example, *P. falciparum, P. vivax, P. knowlesi, P. yoelii, P. chabaudi, P. reichenowi*, and *P. gallinaceum*, is readily available in public databases such as the National Center for Biotechnology Information (www.ncbi.nlm.nih.gov), the *Plasmodium* Genome Database (www.plasmodb.org), and the Sanger Institute (www.sanger.ac.uk).

CITATIONS

The contents of each of the following publications is incorporated by reference herein.

1. Sachs, J. & Malaney, P. The economic and social burden of malaria. *Nature* 415:680–685 (2002).
2. Kappe, S. H., Kaiser, K. & Matuschewski, K. The *Plasmodium* sporozoite journey: a rite of passage. *Trends Parasitol.* 19:135–143 (2003).
3. Shortt, H. E. & Garnham, P. C. C. Pre-erythrocytic stage in mammalian malaria parasites. *Nature* 161:126 (1948).
4. Hoffman, S. L. Save the children. *Nature* 430:940–941 (2004).
5. Nussenzweig, R. S. et al. Protective immunity produced by the injection of X-irradiated sporozoites of *Plasmodium berghei*. *Nature* 216:160–162 (1967).
6. Hoffman, S. L. et al. Protection of humans against malaria by immunization with radiation-attenuated *Plasmodium falciparum* sporozoites. *J. Infect. Dis.* 185:1155–1164 (2002).
7. Hoffman, S. L. & Doolan, D. L. Malaria vaccines-targeting infected hepatocytes. *Nat. Med.* 6:1218–1219 (2000).
8. Gardner, M. J. et al. Genome sequence of the human malaria parasite *Plasmodium falciparum*. *Nature* 419:498–511 (2002).
9. Carlton, J. M. et al. Genome sequence and comparative analysis of the model rodent malaria parasite *Plasmodium yoelii yoelii*. *Nature* 419:512–519 (2002).
10. Hoffman, S. L. & Luke, T. G. Method for the prevention of malaria. WO 2004/045559 A2.
11. Matuschewski, K., J. Ross, S. M. Brown, K, Kaiser, V. Nussenzweig, and S. H. I. Kappe. Infectivity-associated changes in the transcriptional repertoire of the malaria parasite sporozoite stage. *J. Biol. Chem.* 277:41948–41953 (2002).
12. Kaiser, K., Matuschewski, K., Camargo, N., Ross, J. & Kappe, S. H. Differential transcriptome profiling identifies *Plasmodium* genes encoding pre-erythrocytic stage-specific proteins. *Mol. Microbiol.* 51:1221–1232 (2004).
13. V. Thathy and R. Ménard, Gene targeting in *Plasmodium berghei*, in Methods in Molecular Medicine, Vol. 72: Malaria Methods and Protocols, D. L. Doolan, Ed., Humana Press, 2002.
14. Noonpakdee, W., et al., Inhibition of *Plasmodium falciparum* proliferation in vitro by antisense oligodeoxynucleotides against malarial topoisomerase II, *Biochem Biophys Res Commun.* 302(4):659–64, 2003.
15. Gardiner, D. L., et al., Inhibition of *Plasmodium falciparum* clag9 gene function by antisense RNA, *Mol Biochem Parasitol.* 110(1):33–41, 2000
16. Al-Olayan, E. M., et al., Complete development of mosquito phases of the malaria parasite in vitro, *Science* 295:677–679, 2002.
17. Meis, J. F. et al. Malaria parasites—discovery of the early liver form. *Nature* 302:424 (1983).
18. Meis, J. F., & J. P. Verhave. Exoerythrocytic development of malarial parasites. *Adv Parasitol* 27:1 (1988).
19. Druilhe, P. L. et al. Immunity to Liver Stages. In Malaria: Parasite Biology, Pathogenesis and Protection. I. W. Sherman, ed. American Society for Microbiology, Washington D.C., P. 513 (1998).
20. Silvie, O., et al. Effects of irradiation on *Plasmodium falciparum* sporozoite hepatic development: implications for the design of pre-erythrocytic malaria vaccines. *Parasite Immunol* 24:221 (2002).
21. Scheller, L. F., & A. F. Azad. Maintenance of protective immunity against malaria by persistent hepatic parasites derived from irradiated sporozoites. *Proc Natl Acad Sci USA* 92:4066 (1995).
22. Rosenberg, R. et al. An estimation of the number of malaria sporozoites ejected by a feeding mosquito. *Trans R Soc Trop Med Hyg* 84:209 (1990).
23. Beier, J. C. et al. Quantitation of malaria sporozoites transmitted in vitro during salivation by wild Afrotropical *Anopheles*. *Med Vet Entomol* 5:71 (1991).
24. Alger, N. E. et al. Sporozoite and normal salivary gland induced immunity in malaria. *Nature* 238:341 (1972).
25. Kappe, S. H., M. J. Gardner, S. M. Brown, J. Ross, K. Matuschewski, J. M. Ribeiro, J. H. Adams, J. Quackenbush, J. Cho, D. J. Carucci, S. L. Hoffman, and V. Nussenzweig. Exploring the transcriptome of the malaria sporozoite stage. *Proc Natl Acad Sci USA* 98:9895 (2001).

26. Le Roch, K. G. et al. Discovery of gene function by expression profiling of the malaria parasite life cycle. *Science* 301:1503 (2003).

27. Florens, L. et al. A proteomic view of the *Plasmodium falciparum* life cycle. *Nature* 419:520 (2002).

28. Guerin-Marchand, C. et al. A liver-stage-specific antigen of *Plasmodium falciparum* characterized by gene cloning. *Nature* 329:164 (1987).

29. Mueller, Ann-Kristin, Mehdi Labaied, Stefan H. I. Kappe, and Kai Matuschewski. Genetically modified *Plasmodium* parasites as a protective experimental malaria vaccine. *Nature* 433:164–167, 13 January 2005. See also: Ménard, R. Knockout malaria vaccine? *Nature* 433:113–114, 13 January 2005; and Waters, A. P. et al. Malaria vaccines: back to the future? *Science* 307:528–530, 28 January 2005.

30. Sibley, L. D. Intracellular parasite invasion strategies. *Science* 304:248–253 (2004).

31. Meis, J. F. et al. Transformation of sporozoites of *Plasmodium berghei* into exoerythrocytic forms in the liver of its mammalian host. *Cell Tissue Res* 241:353–360 (1985).

32. Potocnjak, P. et al. Monovalent fragments (Fab) of monoclonal antibodies to a sporozoite surface antigen (Pb44) protect mice against malarial infection. *J. Exp. Med.* 151:1504–1513 (1980).

33. Tsuji, M. et al. Demonstration of heat-shock protein 70 in the sporozoite stage of malaria parasites. *Parasitol. Res.* 8016–21 (1994).

34. de Koning-Ward, T. F., et al. *Mol. Biochem. Parasitol.* 106:199–212 (2000).

35. Sultan, A. A., et al. TRAP is necessary for gliding motility and infectivity of *plasmodium* sporozoites. *Cell* 90:511–522 (1997).

36. Renia, L. et al. Malaria sporozoite penetration; a new approach by double staining. *J. Immunol. Methods* 112: 201–205 (1988).

37. Dykxhoorn et al. Killing the messenger: short RNAs that silence gene expression. *Nat. Rev. Mol. Cell Biol.* 4:457–67 (2003).

38. Novino & Sharp. The RNAi revolution. *Nature* 430: 161–164 (2004).

39. Reynolds et al. Rational siRNA design for RNA interference. *Nat. Biotechnol.* 22:326–30 (2004).

40. Heidel et al. Lack of interferon response in animals to naked siRNAs. *Nat. Biotechnol.* DOI:10.1038/nbt1038, Nov. 21, 2004.

41. Kumar et al. Characterization and expression of a PPI serine/threonine protein phosphatase (PfPP1) from the malaria parasite, *Plasmodium falciparum*: demonstration of its essential role using RNA interference. *Malar. J.* 1(1):5 (2002).

42. McRobert & McConkey. RNA interference (RNAi) inhibits growth of *Plasmodium falciparum*. *Mol. Biochem. Parasitol.* 119(2):273–8 (2002).

43. Malotra et al. Double-stranded RNA-mediated gene silencing of cysteine proteases (falcipain-1 and -2) of *Plasmodium falciparum*. *Mol. Microbiol.* 45(5):1245–54 (2002).

44. Mohmmed et al. In vivo silencing in *Plasmodium berghei*: a mouse malaria model. *Biochem. Biophys. Res. Commun.* 309(3):506–11 (2003).

45. Boutros et al. Genome-wide RNAi analysis of growth and viability in *Drosophila* cells. *Science* 303:832–5 (2004).

46. Kamath et al. Systematic functional analysis of the *C. elegans* genome using RNAi. *Nature* 421:231–7 (2003).

47. Duraising et al. Negative selection of *Plasmodium falciparum* reveals targeted gene deletion by double crossover recombination. *Int. J. Parasitol.* 32(1):81–9 (2002).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for inoculating a vertebrate host against malaria, comprising administering to the host a live *Plasmodium* organism that is genetically engineered to disrupt a gene whose expression is up-regulated in liver stage parasites and whose function is not required for entry into host hepatocytes.

* * * * *